United States Patent [19]

Mariam et al.

[11] Patent Number: 5,087,757

[45] Date of Patent: Feb. 11, 1992

[54] PREPARATION OF ALKYLTHIOETHYLAMINE SALTS

[75] Inventors: Kidisti G. Mariam; James A. Sinclair, both of Pittsburg; Terry L. Wright, Oakland, all of Calif.; Charles D. Gartner, Midland, Mich.

[73] Assignee: The Dow Chemical Company, Midland, Mich.

[21] Appl. No.: 255,210

[22] Filed: Oct. 11, 1988

Related U.S. Application Data

[63] Continuation-in-part of Ser. No. 133,663, Dec. 16, 1987, abandoned, which is a continuation-in-part of Ser. No. 917,129, Oct. 9, 1986, abandoned.

[51] Int. Cl.⁵ .......................................... C07C 323/25
[52] U.S. Cl. .................................................. 564/501
[58] Field of Search ........................................ 564/501

[56] References Cited

U.S. PATENT DOCUMENTS 2,930,815  3/1960  Nedwick et al. ............... 564/501
3,821,405  6/1974  Kalopissis et al. ............. 424/319

OTHER PUBLICATIONS

Komoi and Saeki, Yukagaku, 20, 887–90 (1971).
March, *Advanced Organic Chemistry: Reactions, Mechanisms, and Structure*, pp. 587–588.
Turk et al., J. Org. Chem., 27, 2846 (1962).

*Primary Examiner*—Jane T. Fan
*Assistant Examiner*—Ba K. Trinh

[57] ABSTRACT

Alkylthioethylamine salts are prepared by reacting certain alkenes with mercaptoethylamine salts in a glycol or glycol ether solvent in the presence of a free radical initiator. The product mixtures obtained are useful as antimicrobials as is or after the addition of inert formulation additives.

17 Claims, No Drawings

PREPARATION OF ALKYLTHIOETHYLAMINE SALTS

CROSS-REFERENCE TO RELATED APPLICATIONS

This application is a continuation-in-part of Ser. No. 133,663, filed Dec. 16, 1987 now abandoned, which in turn is a continuation-in-part of Ser. No. 917,129, filed Oct. 9, 1986, now abandoned.

BACKGROUND OF THE INVENTION

Alkylthioethylamines and their salts are known to be useful as antimicrobials and/or corrosion inhibitors (e.g., see U.S. Pat. No. 3,524,719, and Komori and Saeki, Yukagaku, 20, 887–890 (1971)). Certain known methods for preparing alkylthioethylamine salts have several disadvantages such as use of flammable solvents and the requirement of several steps. It would be desirable to have a method that is simple, efficient and economical for preparing alkylthioethylamine salts.

SUMMARY OF THE INVENTION

It has now been found that alkylthioethylamine salts can be formed in a single step process. The process of the present invention is, therefore, simple, efficient, and economical. The process of the present invention also provides substantially increased yields of desired product as compared to the known processes. More specifically, the process of the present invention concerns the reaction of a suitable alkene with a suitable mercaptoethylamine salt to form the desired product, i.e., an alkylthioethylamine salt. The process can be illustrated by the following reaction scheme:

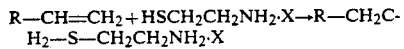

$$R-CH=CH_2 + HSCH_2CH_2NH_2 \cdot X \rightarrow R-CH_2CH_2-S-CH_2CH_2NH_2 \cdot X$$

wherein
R is an alkyl moiety, and
X is a suitable acid.

As used herein in the specification and claims the term "alkyl" refers to a straight chain alkyl of 2 to 20 carbon atoms, a branched alkyl of 3 to 20 carbon atoms or a cyclic alkyl of 3 to 20 carbon atoms. It is preferred that R is an alkyl of 4 to 12 carbon atoms and most preferred that R is an alkyl of 6 to 10 carbon atoms. It is also preferred that R is a straight chain alkyl.

The products formed by the process of the present invention are useful as antimicrobials and/or as corrosion inhibitors.

The process of the present invention is carried out in one or more solvents selected from propylene glycol, dipropylene glycol, propylene glycol methyl ether, dipropylene glycol methyl ether, ethylene glycol diethylene glycol, triethylene glycol, tetraethylene glycol, and combinations of these solvents with water, in the presence of a free radical catalyst, under conditions at which the desired product is formed in greater than 90 percent yield as a mixture in said solvents The reaction mixture containing the desired product can be used directly as an antimicrobial or can be combined with inert formulation ingredients to obtain a mixture suitable for use as an antimicrobial, in either case obviating the need for isolation of the desired product and subsequent formulation in a separate process.

DETAILED DESCRIPTION OF THE INVENTION

The process of the present invention is carried out in the presence of a suitable catalyst. Suitable catalysts are free radical initiators capable of catalyzing the reaction of the alkene and the mercaptoethylamine salt to form the desired product. More specifically, preferred suitable catalysts are hydrogen peroxide, an organic peroxide, and Vazo initiators (azobisnitriles, available from DuPont, Wilmington, DE) such as azobispropionitrile. In addition, it is contemplated that any combination and or mixtures of the suitable catalysts are within the scope of the present invention. The most preferred suitable catalyst is hydrogen peroxide.

As appreciated by those skilled in the art, the reaction conditions can be varied as long as the desired product is formed in greater than 90 percent yield. Yields of greater than about 95 percent are generally obtained and yields of greater than 98 percent are possible. The temperature will vary depending upon the specific starting compounds and specific catalyst and solvent as well as the other reaction conditions such as the duration of the reaction, the size of the reactor, molar ratio of reactants, and the like. However, a typical, preferred temperature range for the process of the present invention is between about 25° and about 130° C.; a more preferred temperature range is between about 40° and about 100° C.; and a most preferred temperature range is between about 50° and about 80° C.

As in the case of temperature, the molar proportion of reactants and catalyst, as well as the duration of the reaction, will vary depending upon the specific reactants, catalyst and other reaction conditions. Typically, the reaction takes place immediately on contact of the reagents and catalyst. A post-contact reaction time of up to about 6 hours may be required.

A typical preferred molar ratio of reactants (i.e., the alkene and the mercaptoethylamine salt) is approximately equimolar; however, the reaction can be run using excess alkene or excess mercaptoethylamine salt. The amount of catalyst required for the process of the present invention is a catalytic amount; that is, an amount of the suitable catalyst that will catalyze the reaction of the alkene with the alkylthioethylamine salt to form the desired alkylthioethylamine salt. Typically a preferred catalytic amount of catalyst is between about 0.001 and 0.5 mole of catalyst per mole of alkene reactant, preferably between about 0.003 and about 0.35 mole.

The process of the present invention is carried out in the presence of suitable solvents. Suitable solvents include ethylene glycol, propylene glycol, propylene glycol methyl ether, dipropylene glycol methyl ether, diethylene glycol, triethylene glycol, tetraethylene glycol and dipropylene glycol, and mixtures of these solvents with water. These solvents and solvent mixtures are characterized by being low in flammability and by having appreciable capacity to dissolve the reactants and products. They are useful formulation solvents for antimicrobial products. Preferred solvents include propylene glycol and tetraethylene glycol, each optionally in combination with water.

The reactants and catalyst can be combined in any order, but is often preferred to add the alkene and catalyst to a mixture containing solvent and the mercaptoethylamine salt. This can be done rapidly or over an extended period of time. It is often convenient to conduct the process in a continuous manner, generally by continuously adding the alkene, mercaptoethylamine salt, solvent, and catalyst to a reactor. The product can be removed from the reactor continuously or the addition of reagents concluded when the reactor is appropriately full.

After the desired product is obtained as a reaction mixture, the reaction mixture can be used, substantially unaltered for antimicrobial end uses, such as application to a cooling tower. However, after the desired product is obtained as a reaction mixture, said mixture can be optionally diluted with water to yield an aqueous solution. An antifoaming agent can also optionally be added to the reaction mixture (now an end use formulation) to reduce or suppress foaming. Acetic or propionic acid can be added to promote solubility. Other common formulation inert ingredients can also be added to obtain a formulation mixture suitable for use as an antimicrobial. Alternately, the reaction mixture can be diluted with an appropriate organic solvent to precipitate the desired product.

The suitable acid (designated herein as "X") can be a wide variety of acids) which form acid salts with the mercaptoethylamine and the alkylthioethylamine of the present invention. Typical preferred suitable acids are HCl, HNO$_3$, HBr, H$_3$PO$_4$, H$_2$SO$_4$ or other mineral acids; or weaker acids such as acetic, propionic, butyric, glycolic, or other monofunctional or polyfunctional carboxylic acids. A preferred suitable acid is HCl.

The process of the present invention proceeds in such a manner such that a greater than 90 percent yield of the desired product is obtained.

Although not necessary, it is usually preferred to reduce the amount of gases (such as oxygen) that can possibly interfere with the reaction process. Therefore, it is preferred to perform the process of the present invention in the presence of a substantially inert gas such as argon, nitrogen, and the like. A preferred inert gas is nitrogen. Also preferred, but not necessary, is that the reaction process of the present invention proceed with mechanical or physical agitation, such as stirring, to facilitate contact of the reactants.

The reactants, solvents and catalysts of the present invention are commercially available. It is often convenient to purchase and use in the process an aqueous solution of the mercaptoethylamine salt.

The present invention is further illustrated by the following examples: however, these examples should not be interpreted as a limitation upon the scope of the present invention.

EXAMPLE 1

A five liter (l) three necked flask, fitted with a mechanical stirrer and a thermometer, is charged with mercaptoethylamine hydrochloride (469 grams (g)) and propylene glycol (1000g). The flask is purged with nitrogen, and the mixture is heated to 50° C with stirring. 1-Decene (555g) and 3 percent hydrogen peroxide catalyst (15 milliliters (ml)) are added to the flask over about 40 minutes by an addition funnel or metering pump. The reaction exotherms to about 70° C. and is maintained at about 60° to 70° C. for about 1.5 hours after addition of the decene. The reaction mixture is then cooled to about 30° C. and diluted with water (4.6 kilograms (Kg)) to give a solution containing 15 percent decylthioethylamine hydrochloride by weight (about 100 percent yield).

EXAMPLE 2

To the solution obtained from Example 1, 0.6g of Dow Corning Q7-2243 LVA Compound (or other antifoaming agent) is added to obtain a formulation suitable for use as an antimicrobial.

EXAMPLE 3

Mercaptoethylamine hydrochloride (227 g of 75 percent aqueous solution of 98 percent purity, 1.47 moles) and 190 g of propylene glycol were combined in a flask and heated to 65° C. with stirring. To this was added over about a 1 hour period 219 g of 96 percent purity decene (1.5 moles) and about 7 ml of 3 percent hydrogen peroxide (0.006 mole). The mixture was stirred at about 65° C. for an additional 3.5 hours during which time another 15 ml of 3 percent hydrogen peroxide (0.013 mole) was added. The mixture was allowed to cool and stand overnight and was then assayed using a standardized high pressure liquid chromatographic analysis method. A total of 373 g of decylthioethylamine hydrochloride was found to be present, which is 99.7 percent of the theoretical yield.

EXAMPLE 4

Mercaptoethylamine hydrochloride (cysteamine hydrochloride, 231 g of a 75 percent aqueous solution, 1.5 mol) was combined with 420 g of tetraethylene glycol in a reaction vessel and the mixture was blanketed with nitrogen and heated to 65° C. Decene (209 g, 1.5 mol) and hydrogen peroxide (8.25 g of 6.3 wt. percent aqueous solution, 0.015 mol) were added slowly with stirring, the decene over a 20 minute period and the hydrogen peroxide over a 55 minute period. The product mixture obtained was analyzed by gas-liquid chromatography and high pressure liquid chromatography and found to contain decylthioethylamine hydrochloride as the only observable reaction product along with unreacted mercaptoethylamine hydrochloride (about 6.5 percent of that added), a trace of unreacted decene, and the bis-2-aminoethyl disulfide dihydrochloride present in the starting materials. The yield was, accordingly, about 93.5 percent of theory.

What is claimed is:

1. A process for the preparation of a product of the formula $$R-CH_2CH_2-S-CH_2CH_2NH_2 \cdot X$$

wherein
R is a C$_2$–C$_{20}$ alkyl moiety, and
X is a suitable acid,
which comprises contacting a compound of the formula $$R-CH=CH_2$$

where
R is as previously defined with a compound of the formula $$HSCH_2CH_2NH_2 \cdot X$$

wherein X is as previously defined, in the presence of one or more solvents selected from the group consisting of propylene glycol, dipropylene glycol, propylene glycol methyl ether, dipropylene glycol methyl ether, ethylene glycol, diethylene glycol, triethylene glycol, and tetraethylene glycol, and combinations thereof with water, in the presence of a catalytic amount of a free radical initiator at temperatures between about 25° C. and about 300° C. so as to obtain said product in a yield of at least 90 percent as a mixture in said solvent.

2. The process of claim 1 wherein R is alkyl of 4 to 12 carbon atoms.

3. The process of claim 2 wherein R is a straight chain alkyl of 6 to 10 carbon atoms.

4. The process of claim 1 wherein the free radical initiator is selected from the group consisting of hydrogen peroxide, an organic peroxide, and an azobisnitrile.

5. The process of claim 4 wherein the suitable catalyst is hydrogen peroxide.

6. The process of claim 1 wherein the solvent is propylene glycol or a mixture thereof with water.

7. The process of claim 1 wherein the solvent is tetraethylene glycol or a mixture thereof with water.

8. The process of claim 1 wherein the suitable acid is hydrochloric acid.

9. The process of claim 1 wherein the reaction temperature is between about 40° and about 100° C.

10. The process of claim 9 wherein the reaction temperature is between about 50° and about 80° C.

11. The process of claim 1 wherein the mixture of the product obtained is further diluted with water.

12. A process of claim 1 wherein the mixture is further combined with inert formulation ingredients so as to produce a mixture suitable for use as an antimicrobial.

13. The process of claim 1 wherein the molar ratio of reactants is approximately equimolar.

14. The process of claim 1 wherein said catalytic amount is between about 0.001 and 0.5 mole of catalyst per mole of alkene reactant.

15. The process of claim 14 wherein said catalytic amount is between about 0.003 and about 0.35 mole of catalyst per mole of alkene reactant.

16. The process of claim 1 wherein said process is carried out in the presence of a substantially inert gas.

17. The process of claim 2 wherein the free radical initiator is hydrogen peroxide, the solvent is propylene glycol or tetraethylene glycol, each optionally in combination with water, the suitable acid is hydrochloric acid, the temperature is between about 50° and about 80° C., and the reaction mixture is further combined with inert formulation ingredients so as to produce a mixture suitable for use as an antimicrobial.

* * * * *